United States Patent [19]

Grasselli et al.

[11] Patent Number: 4,503,001
[45] Date of Patent: Mar. 5, 1985

[54] PROCESS FOR THE MANUFACTURE OF ACRYLONITRILE AND METHACRYLONITRILE

[75] Inventors: Robert K. Grasselli, Garfield Heights; Arthur F. Miller, Cleveland; Harley F. Hardman, Lyndhurst, all of Ohio

[73] Assignee: Standard Oil Company (Indiana), Cleveland, Ohio

[21] Appl. No.: 373,904

[22] Filed: May 3, 1982

Related U.S. Application Data

[63] Continuation of Ser. No. 748,609, Dec. 7, 1976, abandoned, which is a continuation of Ser. No. 85,722, Oct. 30, 1970, abandoned.

[51] Int. Cl.$^3$ ............................................. C07C 120/14
[52] U.S. Cl. .................................................... 260/465.3
[58] Field of Search ...................................... 260/465.3

[56] References Cited

U.S. PATENT DOCUMENTS

| | | | |
|---|---|---|---|
| 3,205,280 | 9/1965 | Wattimena et al. | 260/680 |
| 3,226,422 | 12/1965 | Sennewald et al. | 260/465.3 |
| 3,280,166 | 10/1966 | Callahan et al. | 260/465.3 |
| 3,321,411 | 5/1967 | Young et al. | 260/465.3 X |
| 3,324,166 | 6/1967 | Sennewald et al. | 260/465.3 |
| 3,340,291 | 9/1967 | Barclay et al. | 260/465.3 |
| 3,346,513 | 10/1967 | Hadley | 260/465.3 |
| 3,346,617 | 10/1967 | Hiroki et al. | 260/465.3 |
| 3,414,631 | 12/1968 | Grasselli et al. | 260/465.3 |
| 3,415,886 | 12/1968 | McClellan | 252/437 |
| 3,454,630 | 7/1969 | Yamaguchi et al. | 252/437 |
| 3,621,072 | 11/1971 | Watanabe et al. | 260/681 |
| 3,642,930 | 2/1972 | Grasselli et al. | 260/465.3 X |

FOREIGN PATENT DOCUMENTS 41-11847  6/1966  Japan .
973565  10/1964  United Kingdom .

*Primary Examiner*—Joseph Paul Brust
*Attorney, Agent, or Firm*—Charles S. Lynch; John E. Miller, Jr.; Larry W. Evans

[57] ABSTRACT

Monoolefins such as propylene and isobutylene are converted to the corresponding unsaturated nitriles, acrylonitrile and methacrylonitrile, respectively, by reacting a mixture of the olefin, ammonia, and a molecular oxygen-containing gas in the presence of a catalyst containing the oxides of iron, bismuth, molybdenum, and cobalt or nickel or both, and optionally an oxide of at least one element selected from the group consisting of the alkali metals, rare earth metals, tantalum and niobium, and optionally one or more of the oxides of the elements selected from the group consisting of phosphorus and arsenic.

44 Claims, No Drawings

PROCESS FOR THE MANUFACTURE OF ACRYLONITRILE AND METHACRYLONITRILE

This is a continuation of application Ser. No. 748,609, filed Dec. 7, 1976, now abandoned, which in turn is a continuation of application Ser. No. 85,722 filed Oct. 30, 1970, now abandoned.

This invention relates to a process for the catalytic oxidation of olefin-ammonia mixtures to unsaturated nitriles, and more particularly to the oxidation of propylene-ammonia to acrylonitrile and isobutylene-ammonia to methacrylonitrile. The oxidation is conducted in the presence of a catalyst having the formula:

$$A_a B_b C_c Fe_d Bi_e Mo_f O_x$$

wherein A is at least one element selected from the group consisting of an alkali metal, a rare earth metal, tantalum and niobium, B is one or more of the elements selected from the group consisting of nickel and cobalt, C is phosphorus or arsenic or both, and wherein (a) and (c) are numbers from 0 to 3, (b) is a number from 0.1 to 20, (d) is a number from 0.1 to 8, (e) is a number from 0.1 to 6, (f) is a number from 8 to 16, and (x) is a number determined by the valence requirements of the other elements present.

The catalysts of this invention have a high activity for the production of unsaturated nitriles at a relatively low reaction temperature. This high activity at a low reaction temperature is surprising in view of U.S. Pat. No. 2,904,580 issued Sept. 15, 1959, which discloses a process for the production of acrylonitrile from propylene and ammonia in the presence of a catalyst selected from the group consisting of bismuth, tin and antimony salts of molybdic and phosphomolybdic acids and bismuth phosphotungstate, and U.S. Pat. No. 3,226,422 issued Dec. 28, 1965, which discloses a catalyst comprising the oxides of iron, bismuth, molybdenum, and phosphorus for the production of unsaturated nitriles from olefinammonia mixtures.

In addition to high activity for nitrile production, the catalyst employed in the process of this invention has a number of other important advantages that contribute greatly to the efficient and economic operation of the process. The catalyst has excellent redox stability under the reaction conditions of the process. This permits the use of low process air to olefin ratios and high weight hourly space velocities. The catalyst exhibits efficient ammonia utilization thus greatly reducing the amount of unreacted ammonia appearing in the reactor effluent and thus lowering the amount of sulfuric acid required to neutralize the ammonia in the effluent. The foregoing advantages are accompanied by improvements in the recovery section operation and pollution control resulting from the lowering of polymer waste products that are formed. The catalyst performs optimally at a lower reactor temperature than is normally employed for this type of reaction with per pass conversions to the nitrile product as high as 80 percent and above. Use of lower operating temperatures favors longer catalyst life and minimizes effluent problems such as afterburning. Ease of catalyst preparation and lower cost of the essential catalytic components are additional benefits that can be realized with the use of the catalyst of this invention.

The reactants employed in producing the unsaturated nitriles of this invention are oxygen, ammonia, and an olefin having only three carbon atoms in a straight chain such as propylene or isobutylene, or mixtures thereof.

The olefins may be in admixture with paraffinic hydrocarbons, such as ethane, propane, butane and pentane; for example, a propylene-propane mixture may constitute the feed. This makes it possible to use ordinary refinery streams without special preparation. Likewise, diluents such as nitrogen and the oxides of carbon may be present in the reaction mixture without deleterious effect.

In its preferred aspect, the process comprises contacting a mixture comprising propylene or isobutylene, ammonia and oxygen with the catalyst at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 4:1 and a ratio of about 1:1 to 3:1 is preferred.

The molar ratio of ammonia to olefin in the feed to the reaction may vary between about 0.5:1 to 5:1. There is no real upper limit for the ammonia-olefin ratio, but there is generally no reason to exceed the 5:1 ratio. At ammonia-olefin ratios appreciably less than the stoichiometric ratio of 1:1, various amounts of oxygenated derivates of the olefin will be formed. Outside the upper limit of this range only insignificant amounts of aldehydes and acids will be produced, and only very small amounts of nitriles will be produced at ammonia-olefin ratios below the lower limit of this range. It is unexpected that within the ammonia-olefin range stated, maximum utilization of ammonia is obtained, and this is highly desirable. It is generally possible to recycle any unreacted olefin and unconverted ammonia.

We have found that in many cases water in the mixture fed to the reaction vessel improves the selectivity of the reaction and yield of nitrile. However, reactions not including water in the feed are not to be excluded from this invention, inasmuch as water is formed in the course of the reaction.

In general, the molar ratio of added water to olefin, when water is added, is at least about 0.25:1. Ratios on the order of 1:1 to 4:1 are particularly desirable, but higher ratios may be employed i.e., up to about 10:1.

The reaction is carried out at a temperature within the range of from about 500° to about 1100° F. The preferred temperature range is from about 600° to 900° F.

The pressure at which reaction is conducted is also an important variable, and the reaction should be carried out at about atmospheric or slightly above atmospheric (2 to 3 atmospheres) pressure. In general, high pressures, i.e. about 250 p.s.i.g., are not suitable since higher pressure tend to favor the formation of undesirable by-products.

The apparent contact time is not critical, and contact times in the range of from 0.1 to about 50 seconds may be employed. The optimum contact time will, of course, vary depending upon the olefin being treated, but in general, a contact time of from 1 to 15 seconds is preferred.

In general, any apparatus of the type suitable for carrying out oxidation reactions in the vapor phase may be employed in the execution of this process. The process may be conducted either continuously or intermittently. The catalyst bed may be a fixed-bed employing a large particulate or pelleted catalyst or, in the alternative, a so-called "fluidized" bed of catalyst may be employed. The fluid reactor may comprise an open column or the reactor may contain a plurality of perforated trays stacked horizontally throughout the length of the column, as described in U.S. Pat. No. 3,230,246 issued Jan. 18, 1966.

The reactor may be brought to the reaction temperature before or after the introduction of the reaction feed mixture. However, in a large scale operation it is preferred to carry out the process in a continuous manner, and in such a system the circulation of the unreacted olefin is contemplated. Periodic regeneration or reactivation of the catalyst is also contemplated, and this may be accomplished, for example, by contacting the catalyst with air at an elevated temperature.

The products of the reaction may be recovered by any of the methods known to those skilled in the art. One such method involves scrubbing the effluent gases from the reactor with cold water or an appropriate solvent to remove the products of the reaction. If desired, acidified water can be used to absorb the products of reaction and neutralize unconverted ammonia. The ultimate recovery of the products may be accomplished by conventional means. The efficiency of the scrubbing operation may be improved when water is employed as the scrubbing agent by adding a suitable wetting agent in the water. Where molecular oxygen is employed as the oxidizing agent in this process, the resulting product mixture remaining after the removal of the nitriles may be treated to remove carbon dioxide with the remainder of the mixture containing the unreacted olefin and oxygen being recycled through the reactor. In the case where air is employed as the oxidizing agent in lieu of molecular oxygen, the residual product after separation of the nitriles and other carbonyl products may be scrubbed with a non-polar solvent, e.g., a hydrocarbon fraction in order to recover unreacted olefin, and in this case the remaining gases may be discarded. The addition of a suitable inhibitor to prevent polymerization of the unsaturated products during the recovery steps is also contemplated.

The catalyst useful in the process of the present invention is the homogeneous mixture, compound or possibly a complex of some unknown physical or chemical nature of the oxides of iron, bismuth, and molybdenum, plus nickel or cobalt or both, and optionally phosphorus and or arsenic, an alkali metal, a rare earth metal, niobium or tantalum or both. The composition is conveniently expressed in the following empirical formula:

$A_aB_bC_cFe_dBi_eMo_fO_x$ wherein A is at least one element selected from the group consisting of an alkali metal, a rare earth metal, tantalum and niobium, B is one or more of the elements selected from the group consisting of nickel and cobalt, C is phosphorus or arsenic or both, and wherein (a) and (c) are numbers of from 0 to 3, (b) is a number from 0.1 to 20, (d) is a number from 0.1 to 8, (e) is a number from 0.1 to 6, (f) is a number from 8 to 16, and (x) is a number determined by the valence requirements of the other elements present. A preferred catalyst composition is one in which A is potassium, samarium, or tantalum, and the atom ratios of the elements in the foregoing empirical formula are within the range wherein (a) is from 0 to 1, (b) is from 1 to 12, (c) is from 0.1 to 1.5, (d) and (e) each is from 0.5 to 4, and (f) is about 12.

The catalyst of this invention may be prepared by any of the numerous methods of catalyst preparation which are known to those skilled in the art. For example, the catalyst may be manufactured by co-gelling the various ingredients. The co-gelled mass may then be dried and ground to an appropriate size. Alternately, the co-gelled material may be slurried and spray dried in accordance with conventional techniques. The catalyst may be extruded as pellets or formed into spheres in oil as is well known in the art. Alternatively, the catalyst components may be mixed with the support in the form of the slurry followed by drying, or may be impregnated on silica or other supports.

The alkali metal may be introduced into the catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalyst one may use any compound of iron which, upon calcination, will result in the oxides. As with the other elements, water-soluble salts are preferred for the ease with which they may be uniformly dispersed within the catalyst. Most preferred is ferric nitrate. Cobalt, nickel, and the rare earth metals are similarly introduced.

To introduce the molybdenum component, any molybdenum oxide such as the dioxide, trioxide, pentoxide, or sesquioxide may be used; more preferred is a hydrolyzable or decomposable molybdenum salt such as a molybdenum halide. A preferred starting material is ammonium heptamolybdate.

Arsenic may be introduced as orthoarsenic acid. Other elements may be introduced, starting with the metal, oxidizing the metal with an oxidizing acid such as nitric acid, and then incorporating the nitrate into the catalyst. Generally, the nitrates are readily available and form a very convenient starting material.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxides of the instant catalyst.

The catalyst can be employed without a support and will display excellent activity. It also can be combined with a support, and preferably at least 10 percent up to about 90 percent of the supporting compound by weight of the entire composition is employed in this event. Any known support materials can be used, such as, for example, silica, alumina, zirconia, titania, alundum, silicon carbide, alumina-silica, and the inorganic phosphates, silicates, aluminates, borates and carbonates which are stable under the reaction conditions to be encountered in the use of the catalyst.

The catalytic activity of the system is enhanced by heating at an elevated temperature. Generally, the catalyst mixture is dried and heated at a temperature of from about 750° to about 1850° F., preferably at about 900° to 1300° F., for from one to twenty-four hours or more. If activity then is not sufficient, the catalyst can be further heated at a temperature above about 1000° F., but below a temperature deleterious to the catalyst at which it is melted or decomposed. Usually this limit is not reached before 2000° F., and in some cases this temperature can be exceeded.

In general, the higher the activation temperature, the less time required to effect activation. The sufficiency of activation at any given set of conditions is ascertained by a spot test of a sample of the material for catalytic activity. Activation is best carried out in an open chamber, permitting circulation of air or oxygen, so that any oxygen consumed can be replaced.

Further, pre-treatment or activation of the catalyst before use with a reducing agent such as ammonia in the presence of a limited amount of air at a temperature in the range of 550° to 900° F. is also beneficial.

A preferred method of preparing the catalyst of this invention will be described hereinafter in connection with the working examples of the invention.

A more complete description of the process of the present invention can be obtained from the following examples.

EXAMPLES 1 TO 14

The catalysts employed in the fixed-bed reactor in Examples 1 to 14 were prepared by one of the several following methods. A catalyst having the composition 82.5 wt. %-$Ni_{10.5}FeBiPMo_{12}O_{57}$-17.5 wt. %-$SiO_2$ (Example 2) was prepared as follows:

229.3 grams of $(NH_4)_6Mo_7O_{27}.4H_2O$ were dissolved in water with a minimum amount of heating. 12.5 grams of $H_3PO_4$ (85 wt. %) and 228 grams of Du Pont Ludox AS (30 wt. %) colloidal silica sol were added in succession with stirring. 330.4 grams of $Ni(NO_3)_2.6H_2O$ dissolved in water were added to the slurry and stirred for 15 minutes. 43.8 grams of $Fe(NO_3)_3.9H_2O$ dissolved in water were added to this slurry followed by the addition of 52.5 grams of $Bi(NO_3)_3.5H_2O$ dissolved in water containing 5.3 cc of concentrated $HNO_3$ (60 wt.%). The slurry was stirred constantly for about 15 minutes.

The slurry was then spray dried and the powder obtained from the spray drier was further dried in an oven at 230° F. for 16 hours. The resulting dry powder was well mixed with 1 wt.% graphite and compacted into 1/16"×3/16" pellets with a conventional pelleting machine. The pellets were heated for 5 hours at 446° F. to decompose the nitrates and were then calcined for 20 hours at 1022° F. The pelleted catalyst was crushed and sized to 20-35 Tyler mesh size.

In an alternate method a catalyst having the composition 80 wt.%-$Ni_{4.5}Co_4FeBiAs_{0.5}P_{0.5}Mo_{12}O_{54}$-20 wt.%-$SiO_2$ (Example 4) was prepared by co-gelling the ingredients according to the following procedure:

A mixture of 76.4 grams $(NH_4)_6Mo_7O_{24}.4H_2O$
2.1 grams $H_3PO_4(85\%)$,
2.7 grams $H_3As_3O_4.1/2H_2O$,
85.0 grams $SiO_2$, (Ludox AS, 30% silica sol),
47.2 grams $Ni(NO_3)_2.6H_2O$, and
41.9 grams $Co(NO_3)_2.6H_2O$ was dissolved in water and stirred for 15 minutes. To this slurry was added an aqueous solution containing 14.6 grams of $Fe(NO_3)_3.9H_2O$ and 17.5 grams of $Bi(NO_3)_3.5H_2O$ previously dissolved in 20 cc of a 10% $HNO_3$ solution. The combined mixtures were heated with constant stirring until gel formation occurred. The gel was then dried at approximately 266° F. The resulting catalyst was heat treated at 800° F. for 4 hours, and at 1022° F. for 16 hours, and then was sized to 20-35 Tyler screen mesh.

The reactor employed in examples 1 to 14 was a standard reactor with a fixed catalyst bed. The catalyst volume was about 5 cc and the catalyst mesh size was 20 to 35 Tyler screen mesh. The gases were metered to the reactor with rotameters. The products of the reaction were recovered by scrubbing the effluent gases from the reactor with water and were then analyzed by means of a gas chromatograph.

In the examples 1 to 14 and those listed hereinbelow, the following definition was employed:

Mole percent per pass conversion to unsaturated nitrile =

$$\frac{\text{Mols of nitrile product obtained}}{\text{Mols of olefin fed}} \times 100$$

EXAMPLES 15 TO 18

Examples 15 to 18 were run in a fluid-bed reactor. The fluid catalysts employed in these experiments were prepared as follows:

A catalyst having the composition 50 wt.%-$K_{0.07}Ni_{2.5}Co_{4.5}Fe_3BiP_{0.5}Mo_{12}O_{55}$-50 wt.%-$SiO_2$ (Example 15) was prepared by dissolving 1868.4 grams of $(NH_4)_6Mo_7O_{24}.4H_2O$ in 1500 cc of water (using minimum heating) and then blending with 50.8 grams of 85% $H_3PO_4$. To this solution was added an aqueous solution composed of 1155.1 grams of $Co(NO_3)_2.6H_2O$, 641.1 grams of $Ni(NO_3)_2.6H_2O$ and 500 grams of water. While maintaining vigorous agitation, an aqueous solution of 6.25 grams of $KNO_3$ and 1068.9 grams of $Fe(NO_3)_3.9H_2O$ in 500 cc of water was added to the above. To this was added a solution composed of 427.8 grams of $Bi(NO_3)_3.5H_2O$, 43 cc of 68% $HNO_3$ and 500 cc of water. After addition of 8333.3 grams of 30% silica sol (Du Pont AS Ludox), the slurry was heated with stirring until the solids content was 51.4 wt.%. After blending for several minutes in a Waring blender, the slurry was spray dried in a 4½ foot diameter Bowen spray drier with an inlet temperature of 556° F. and an outlet temperature of 350° F. The microsphereoidal product from the spray drier was put in a furnace at 280° F. The temperature was raised to the 580°-600° F. range over a period of one hour and maintained at this temperature range for seven hours. A final calcination of 24 hours duration at 1020° F. was imposed upon the catalyst prior to charging the material to the fluidized-bed reactor for testing.

An example of the preparation of an attrition-resistant catalyst for use in a fluid-bed reactor and having the same composition as the catalyst described herein above is as follows:

1868.4 grams of $(NH_4)_6Mo_7O_{24}.4H_2O$ was dissolved in 1500 cc of water (using minimum heating) and then blended with 50.8 grams of 85% $H_3PO_4$. To this solution was added an aqueous solution composed of 1155.1 grams of $Co(NO_3)_2.6H_2O$, 641.1 grams of $Ni(NO_3)_2.6H_2O$ and 500 grams of water. While maintaining vigorous agitation, an aqueous solution of 6.25 grams of $KNO_3$ and 1068.9 grams of $Fe(NO_3)_3.9H_2O$ in 500 cc of water was added to the above. To this was added a solution composed of 427.8 grams of $Bi(NO_3)_3.5H_2O$, 43 cc of 68% $HNO_3$ and 500 cc of water. After addition of 4166.7 grams of 30% silica sol (Du Pont AS Ludox), the slurry was heated with stirring until a non-fluid cake was obtained. The solid was then treated at a temperature of 600° F. for a period of 4½ hours. After pulverizing the dry solid mechanically, the 3574 grams of powder were blended with 3971 grams of 30% silica sol (Du Pont AS Ludox) and sufficient water to result in a 52.6 wt.% solids slurry. The blend was ball milled in a porcelain ball mill for 20 hours. The resulting slurry was then spray dried in a 4½ foot diameter Bowen spray drier with an inlet temperature of 550° F. and an outlet temperature of 350° F. The microsphereoidal product from the spray drier was put into a furnace at 280° F. The temperature was raised to 600° F. over a period of one hour and maintained at that temperature for three hours. A final calcination of 24 hours duration at 1020° F. was imposed upon the catalyst prior to changing the material to the fluidized-bed reactor for testing.

The fluid-bed reactor employed in Examples 15 through 18 comprised a reactor column consisting of a 36" length of steel pipe with an I.D. of 1½". In this reactor the air inlet to the column was situated below the inlet for the ammonia and hydrocarbon feeds, and the catalyst volume for this reactor was 650 grams. The procedure followed for product recovery and product analysis was the same as that employed in Examples 1 through 14.

EXAMPLES 19 TO 22

The catalyst preparations and the fixed-bed reactor utilized in these experiments were the same as those employed in Examples 1 through 14.

Comparative ammoxidation reactions were carried out with catalyst compositions disclosed in the prior art references U.S. Pat. No. 2,904,580 and U.S. Pat. No. 3,226,422 and the results are shown in Examples 13 and 14 of Table I and in Examples 20 and 22 of Table III. The data in these tables show that per pass conversions to acrylonitrile and to methacrylonitrile obtained with the catalyst of the present invention are substantially higher than those obtained with the catalysts of the prior art. The data in Table II substantiate the high conversion levels obtained with the catalysts of this invention in a large scale fluid unit.

TABLE I

CONVERSION OF PROPYLENE TO ACRYLONITRILE
Fixed-Bed Reactor

Reaction Temperature: 752° F.   Pre-Run Time: 15 minutes
Contact Time: 2.9 seconds   Run Time: 30 minutes
Feed Ratio (Molar): $C_3^=/NH_3/Air = 1/1.5/11$

| Example No. | Catalyst Composition | (Mole Basis) % Per Pass Conversion to Acrylonitrile |
|---|---|---|
| 1 | 80%-$Co_6FeBiMo_{12}O_{48}$ 20%-$SiO_2$ | 67.4 |
| 2 | 82.5%-$Ni_{10.5}FeBiPMo_{12}O_{57}$ 17.5%-$SiO_2$ | 78.4 |
| 3 | 80%-$Ni_{10.5}FeBiAsMo_{12}O_{57}$ 20%-$SiO_2$ | 66.3 |
| 4 | 80%-$Ni_{4.5}Co_4FeBiAs_{0.5}P_{0.5}Mo_{12}O_{54}$ 20%-$SiO_2$ | 73.9 |
| 5 | 80%-$K_{0.07}Ni_{2.5}Co_{4.5}FeBi_3P_{0.5}Mo_{12}O_{57}$ 20%-$SiO_2$ | 63.8 |
| 6 | 80%-$K_{0.07}Ni_{2.5}Co_{4.5}Fe_2Bi_2P_{0.5}Mo_{12}O_{56}$ 20%-$SiO_2$ | 65.5 |
| 7 | 82.5%-$K_{0.07}Ni_{2.5}Co_{4.5}Fe_3BiP_{0.5}Mo_{12}O_{55}$ 17.5%-$SiO_2$ | 80.0 |
| 8 | 80%-$Ta_{0.2}Ni_{2.5}Co_{4.5}Fe_3BiMo_{12}O_{55.5}$ 20%-$SiO_2$ | 65.4 |
| 9 | 80%-$Sm_{0.1}Ni_{10}Co_{0.3}FeBiPMo_{12}O_{57}$ 20%-$SiO_2$ | 68.3 |
| 10 | 80%-$Sm_{0.1}Ni_{5.25}Co_{5.25}FeBiPMo_{12}O_{57}$ 20%-$SiO_2$ | 64.9 |
| 11 | 50%-$K_{0.07}Ni_{2.5}Co_{4.5}Fe_3BiP_{0.5}Mo_{12}O_{55}$ 50%-$SiO_2$ (attrition resistant) | 67.9 |
| 12 | 100%-$K_{0.07}Ni_{2.5}Co_{4.5}Fe_3BiP_{0.5}Mo_{12}O_{55}$ | 65.4 |
| 13 | 50%-$Bi_9PMo_{12}O_{52}$ 50%-$SiO_2$ | 39.9 |
| 14 | 50%-$Fe_{4.5}Bi_{4.5}PMo_{12}O_{56.5}$- 50%-$SiO_2$ | 41.9 |

TABLE II

CONVERSION OF PROPYLENE TO ACRYLONITRILE
Fluidized-Bed Reactor

| Example No. | Catalyst* Composition | Feed Ratio (Molar) $C_3^=/Air/NH_3$ | Temp. (°F.) | Contact Time (seconds) | % Per Pass Conversion to Acrylonitrile (Mole Basis) |
|---|---|---|---|---|---|
| 15 | A | 1/11.0/1.2 | 762 | 6.0 | 71.9 |
| 16 | B | 1/11.4/1.0 | 763 | 13.0 | 71.3 |
| 17 | B | 1/9.6/1.0 | 763 | 7.0 | 75.4 |
| 18 | B | 1/9.9/1.2 | 780 | 6.7 | 77.7 |

*A = 50%-$(Co_{4.5}Fe_3Ni_{2.5}BiP_{0.5}K_{0.07}Mo_{12}O_{55})$-50% $SiO_2$
B = 82.5%-$(Co_{4.5}Fe_3Ni_{2.5}BiP_{0.5}K_{0.07}Mo_{12}O_{55})$-17.5% $SiO_2$

TABLE III

CONVERSION OF ISOBUTYLENE TO METHACRYLONITRILE
Fixed-Bed Reactor

Reaction Temperature: 716° F.   Contact Time: 2.9 seconds
Feed Ratio (Molar): $IC_4^=/NH_3/Air$ = (1) 1/1.5/11
(2) 1/1.2/10

| Example No. | Catalyst Composition | Feed Ratio | (Mole Basis) % Per Pass Conversion to Methacrylonitrile |
|---|---|---|---|
| 19 | 82.5%-$Ni_{10.5}FeBiPMo_{12}O_{57}$- 17.5%-$SiO_2$ | (1) | 49.8 |
| 20 | 50%-$Fe_{4.5}Bi_{4.5}PMo_{12}O_{56.5}$- 50%-$SiO_2$ | (1) | 34.1 |
| 21 | 82.5%-$K_{0.7}Ni_{2.5}Co_{4.5}Fe_3BiP_{0.5}Mo_{12}O_{55}$- 17.5%-$SiO_2$ | (2) | 69.7 |
| 22 | 50%-$Fe_{4.5}Bi_{4.5}PMo_{12}O_{56.5}$- 50%-$SiO_2$ | (2) | 26.8 |

We claim:

1. In a process for preparing acrylonitrile, methacrylonitrile or a mixture thereof by reacting propylene, isobutylene or a mixture thereof in the vapor phase with a molecular oxygen-containing gas and ammonia in the presence of an oxidation catalyst at a temperature of from about 500° to 1100° F. and at a pressure of about 0.5 to 5 atmospheres, the improvement wherein said oxidation catalyst has the formula:

$$A_a B_b C_c Fe_d Bi_e Mo_f O_x$$

wherein
A is an alkali metal or mixture thereof;
B is at least one element selected from the group consisting of cobalt and nickel; and
C is at least one element selected from the group consisting of phosphorus and arsenic; and
wherein
a is a number greater than 0 to 3;
b is a number from 0.1 to 20;
c is a number from 0 to 3;
d is a number from 0.1 to 8;
e is a number from 0.1 to 6;
f is a number from 8 to 16; and
x is a number determined by the valence requirements of the other elements present.

2. The process of claim 1 wherein said catalyst contains cobalt and nickel.

3. The process of claim 1 wherein said catalyst contains nickel.

4. The process of claim 1 wherein said catalyst contains cobalt.

5. The process of claim 1 wherein said catalyst consists essentially of $A_a B_b C_c Fe_d Bi_e Mo_f O_x$.

6. The process of claim 1 wherein said catalyst consists of $A_a B_b C_c Fe_d Bi_e Mo_f O_x$.

7. The process of claim 1 wherein the temperature is in the range of 600° to 900° F.

8. The process of claim 7 wherein the olefin is propylene.

9. The process of claim 8 wherein the molar ratios of olefin:oxygen:ammonia are within the range of 1:0.5–4:0.5–5.

10. The process of claim 9 wherein said molecular oxygen-containing gas is air.

11. The process of claim 10 wherein said catalyst is supported on a catalyst support.

12. The process of claim 11 carried out in the presence of steam.

13. The process of claim 8 wherein A is at least potassium.

14. The process of claim 8 wherein a is greater than 0 to 1 and f is about 12.

15. The process of claim 14 wherein b is 1 to 12.

16. The process of claim 15 wherein d and e and 0.5 to 4.

17. The process of claim 1 wherein the olefin is isobutylene.

18. In a process for preparing acrylonitrile, methacrylonitrile or a mixture thereof by reacting propylene, isobutylene or a mixture thereof in the vapor phase with a molecular oxygen-containing gas and ammonia in the presence of an oxidation catalyst at a temperature from about 500° to 1100° F. and at a pressure of about 0.5 to 5 atm., the improvement, wherein said oxidation catalyst has the empirical formula:

$$A_a B_b C_c Fe_d Bi_e Mo_f O_x$$

wherein
A is an alkali metal or a mixture thereof;
B is at least one element selected from the group consisting of cobalt and nickel, and
C is at least one element selected from the group consisting of phosphorus and arsenic, and
wherein
a is a number greater than 0 to 3,
b is a number from 0.1 to 20,
c is a number from 0 to 3,
d is a number from 0.1 to 8,
e is a number from 0.1 to 6,
f is a number from 8 to 16, and
x is a number determined by the valence requirement of the other elements present,
said catalyst being made by forming a composition containing all of the elements of said catalyst and thereafter heating said composition at an elevated temperature below a temperature at which said catalyst is melted or decomposed.

19. The process of claim 18 wherein said composition as heated at a first temperature between about 750° F. and about 1850° F. and thereafter heated at a second temperature of about 1000° F. to about 2000° F.

20. The process of claim 19 wherein a is greater than 0 to 1, b is 1 to 12, d and e and 0.5 to 4, and f is about 12.

21. The process of claim 20 wherein d is about 1 to 3.

22. The process of claim 21 wherein b+d is about 10.

23. The process of claim 22 wherein based on 12 atoms of molybdenum, said catalyst contains about 2.5 atoms nickel and about 4.5 atoms cobalt.

24. The process of claim 23 wherein said catalyst further contains about 0.7 atoms potassium and 0.5 atoms phosphorus.

25. The process of claim 18 wherein a is greater than 0 to 1, b is from 1 to 12, d and e each are from 0.5 to 4 and f is about 12.

26. The process of claim 25 wherein d is about 1 to 3.

27. The process of claim 26 wherein b+d is about 10.

28. The process of claim 27 wherein based on 12 atoms of molybdenum, said catalyst contains about 2.5 atoms nickel and about 4.5 atoms cobalt.

29. The process of claim 28 wherein said catalyst further contains about 0.7 atoms potassium and 0.5 atoms phosphorus.

30. The process of claim 29 wherein said reactant is propylene.

31. The process of claim 25 wherein said reactant is propylene.

32. The process of claim 1 wherein based on 12 atoms of molybdenum, said catalyst contains about 0.07 atom potassium, about 0.5 atom phosphorus, about 2.5 atoms nickel, about 4.5 atoms cobalt, about 3 atoms iron and about 1 atom bismuth.

33. The process of claim 1 wherein based on 12 atoms of molybdenum, said catalyst contains about 0.07 atom potassium, about 2.5 atoms nickel, about 4.5 atoms cobalt, about 0.5 atom phosphorus, 1 to 3 atoms iron and about 1 to 3 atoms bismuth.

34. The process of claim 1 wherein A is at least potassium, a is about 0.07 to 1.0, b is 1 to 12, c is 0.1 to 1.5, d is 1 to 3, e is 0.5 to 4 and f is 12.

35. The process of claim 1 wherein A is at least potassium, a is about 0.07 to 1.0, b is 1 to 12, d is 1 to 3, e is 0.5 to 4 and f is 12.

36. The process of claim 1 wherein a is greater than 0 to 1, b is 1 to 12, d is 1 to 3, e is 0.5 to 4, and f is 12.

37. The process of claim 1 wherein b is 1 to 12, d is 1 to 3, e is 0.5 to 4 and f is 12.

38. The process of claim 1 wherein b is 1 to 12 and e is 0.5 to 4.

39. The process of claim 4 wherein A is at least potassium and a is at least 0.07.

40. The process of claim 39 wherein the reactant is propylene.

41. The process of claim 2 wherein A is at least potassium and a is at least about 0.07.

42. The process of claim 41 wherein the reactant is propylene.

43. The process of claim 3 wherein A is at least potassium and a is at least 0.07.

44. The process of claim 4 wherein a is at least about 0.07.

* * * * *

UNITED STATES PATENT AND TRADEMARK OFFICE
CERTIFICATE OF CORRECTION

PATENT NO. : 4,503,001

DATED : March 5, 1985

INVENTOR(S) : Robert K. Grasselli, et al

It is certified that error appears in the above-identified patent and that said Letters Patent is hereby corrected as shown below:

On the title page:

"Arthur F. Miller" has been deleted

"(Indiana)" has been deleted.

Signed and Sealed this

Sixth Day of August 1985

[SEAL]

Attest:

DONALD J. QUIGG

Attesting Officer  Acting Commissioner of Patents and Trademarks